(12) United States Patent
Biedermann

(10) Patent No.: US 10,258,351 B2
(45) Date of Patent: Apr. 16, 2019

(54) BONE PLATE ASSEMBLY WITH GUIDE MEMBER

(75) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 194 days.

(21) Appl. No.: 13/267,900

(22) Filed: Oct. 7, 2011

(65) Prior Publication Data
US 2012/0089192 A1 Apr. 12, 2012

Related U.S. Application Data

(60) Provisional application No. 61/390,869, filed on Oct. 7, 2010.

(30) Foreign Application Priority Data

Mar. 24, 2011 (EP) ..................................... 11159670

(51) Int. Cl.
A61B 17/80 (2006.01)
A61B 17/17 (2006.01)

(52) U.S. Cl.
CPC ...... *A61B 17/1728* (2013.01); *A61B 17/1757* (2013.01); *A61B 17/8057* (2013.01)

(58) Field of Classification Search
CPC ............ A61B 17/7044; A61B 17/7082; A61B 17/7079; A61B 17/8897
USPC ..................................... 606/70, 71, 279–299
See application file for complete search history.

(56) References Cited

U.S. PATENT DOCUMENTS

| 5,127,914 | A | * | 7/1992 | Calderale | A61B 17/746 606/65 |
| 5,520,690 | A | * | 5/1996 | Errico | A61B 17/7037 606/287 |
| 5,628,740 | A | * | 5/1997 | Mullane | 606/307 |
| 6,139,550 | A | * | 10/2000 | Michelson | A61B 17/1604 606/287 |
| 2002/0143338 | A1 | * | 10/2002 | Orbay | A61B 17/68 606/287 |
| 2003/0083667 | A1 | * | 5/2003 | Ralph | A61B 17/1728 606/96 |

(Continued)

FOREIGN PATENT DOCUMENTS

DE 20 2009 012 270 U1 12/2009
EP 1 878 394 A2 1/2008

(Continued)

OTHER PUBLICATIONS

Partial translation of DE 20 2009 012 270 U1.
Extended European Search Report dated Jul. 4, 2011 in priority application EP 11 159 670.6 (in English).

Primary Examiner — Samuel S Hanna
(74) Attorney, Agent, or Firm — Gordon & Jacobson, P.C.

(57) ABSTRACT

A bone plate assembly is provided including a plate member with a top side (1a) and a bottom side (1b), at least one hole (2) extending from the top side (1a) to the bottom side (1b), an insert (3) arranged in the hole, the insert having a through hole (31), a guide member (4) removably arranged in the through hole of the insert, the guide member having a guide channel (40) and an outer surface portion (41) which engages an inner wall portion (32) of the through hole (31) to allow a pivoting movement of the guide member within the insert.

27 Claims, 14 Drawing Sheets

(56) References Cited

U.S. PATENT DOCUMENTS

| | | | |
|---|---|---|---|
| 2004/0267284 A1* | 12/2004 | Parmer | A61B 90/11 |
| | | | 606/130 |
| 2005/0085824 A1* | 4/2005 | Castaneda | 606/98 |
| 2005/0234457 A1* | 10/2005 | James | A61B 17/72 |
| | | | 606/62 |
| 2006/0149250 A1 | 7/2006 | Castaneda et al. | |
| 2006/0241618 A1 | 10/2006 | Gasser et al. | |
| 2009/0048599 A1* | 2/2009 | Hajianpour | A61B 17/6491 |
| | | | 606/59 |
| 2009/0088767 A1 | 4/2009 | Leyden et al. | |
| 2010/0030268 A1* | 2/2010 | Flynn et al. | 606/246 |
| 2010/0063516 A1* | 3/2010 | Parmer et al. | 606/130 |
| 2010/0162552 A1* | 7/2010 | Solar et al. | 29/428 |
| 2013/0012945 A1* | 1/2013 | Chreene et al. | 606/80 |

FOREIGN PATENT DOCUMENTS

| WO | WO/2004/069066 A1 | 8/2004 |
|---|---|---|
| WO | WO/2006/047581 A2 | 5/2006 |
| WO | WO/2008/064211 A1 | 5/2008 |

\* cited by examiner

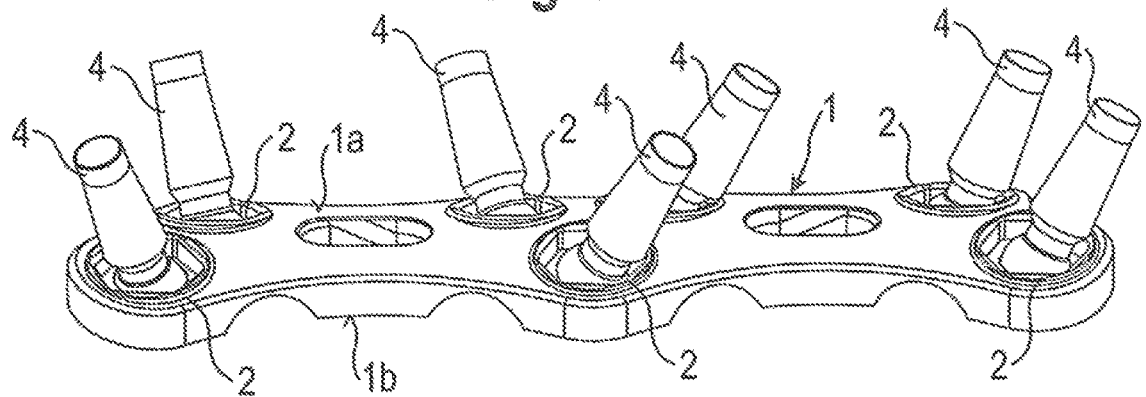
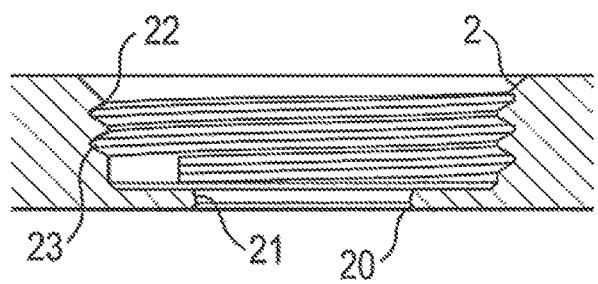
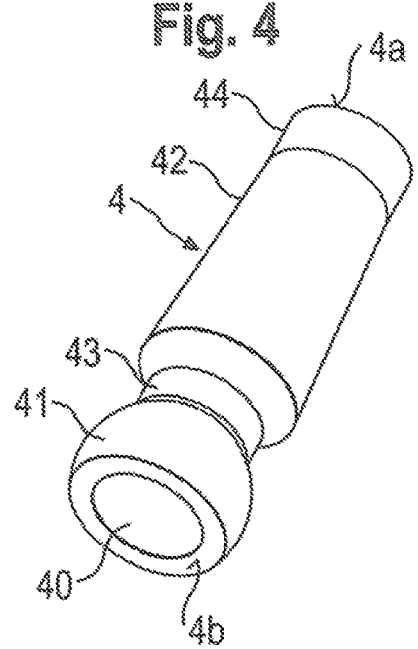
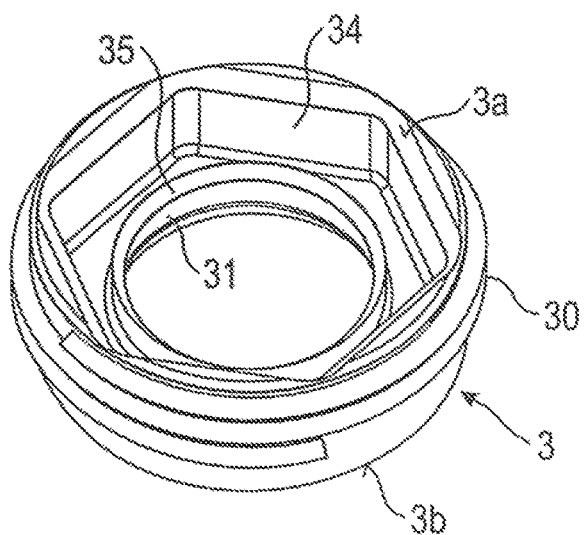

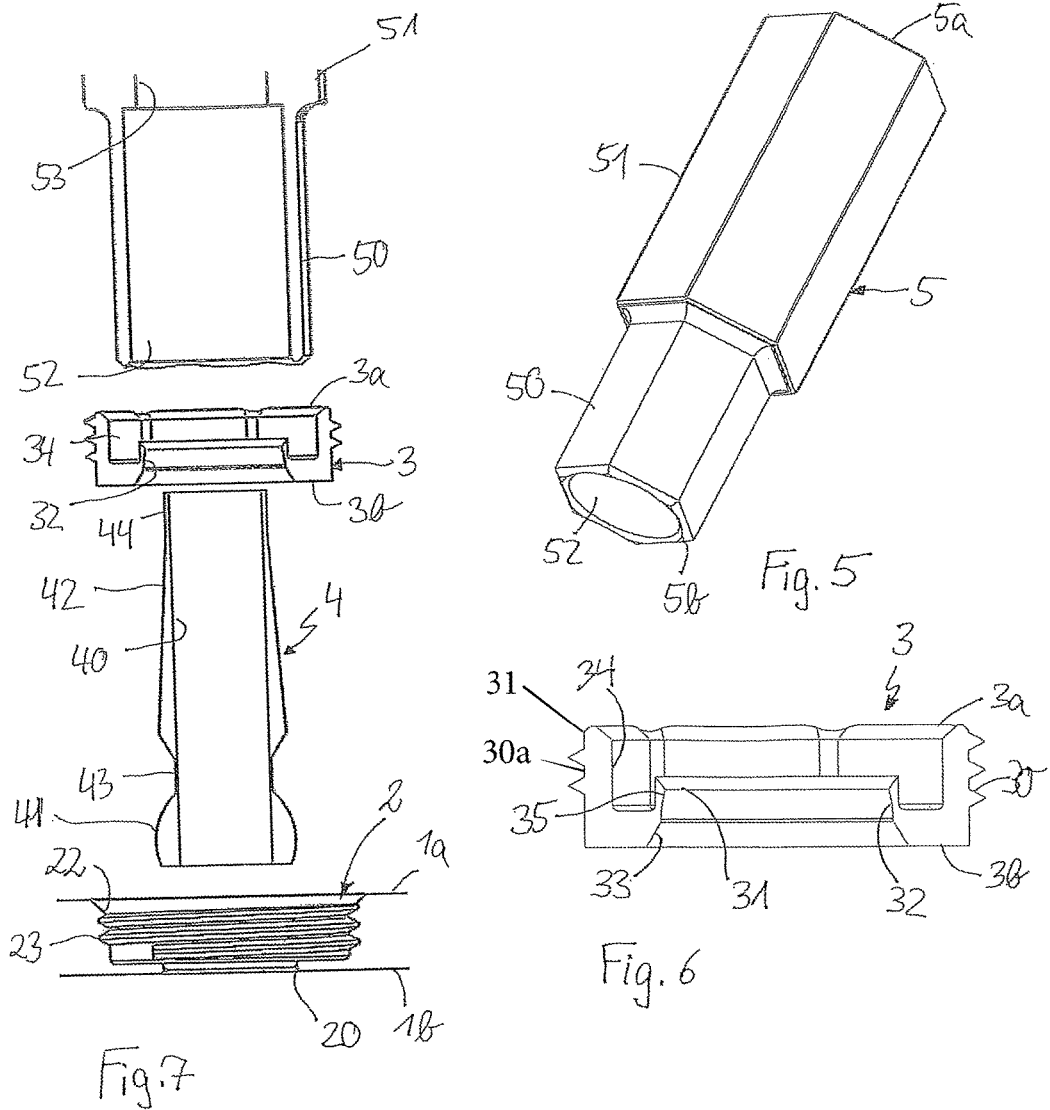

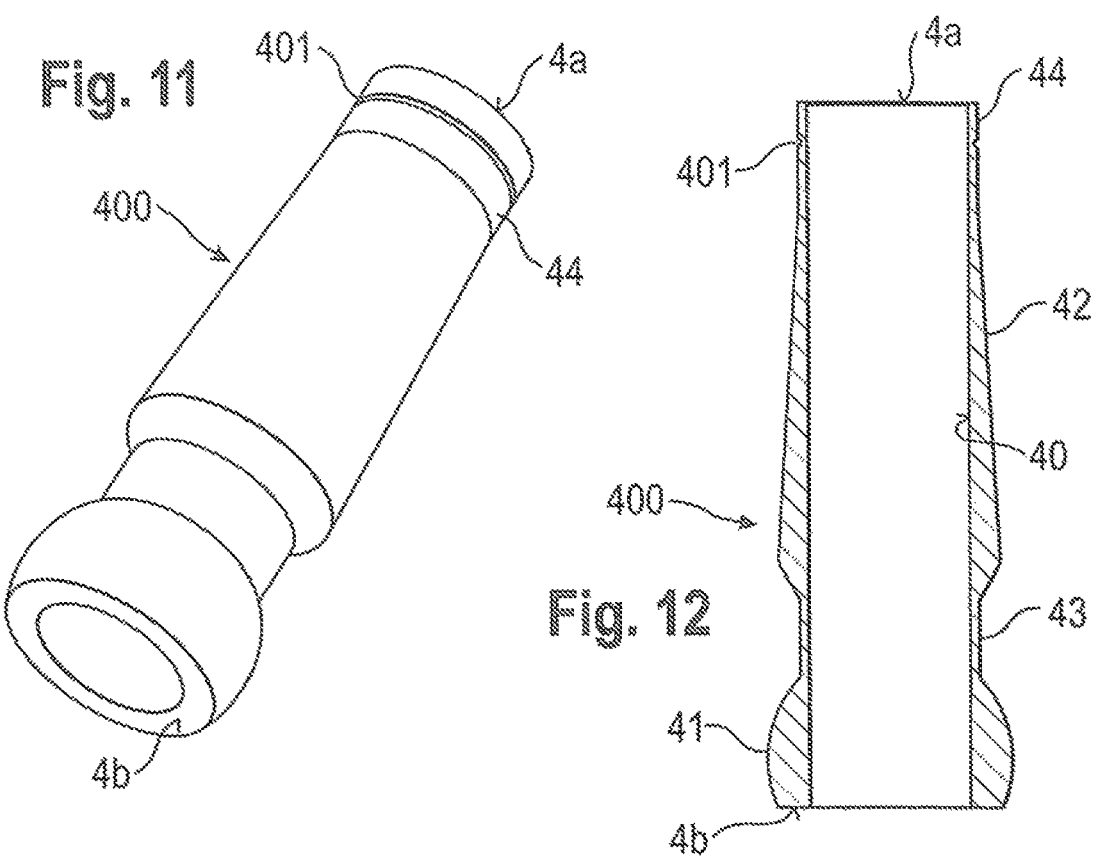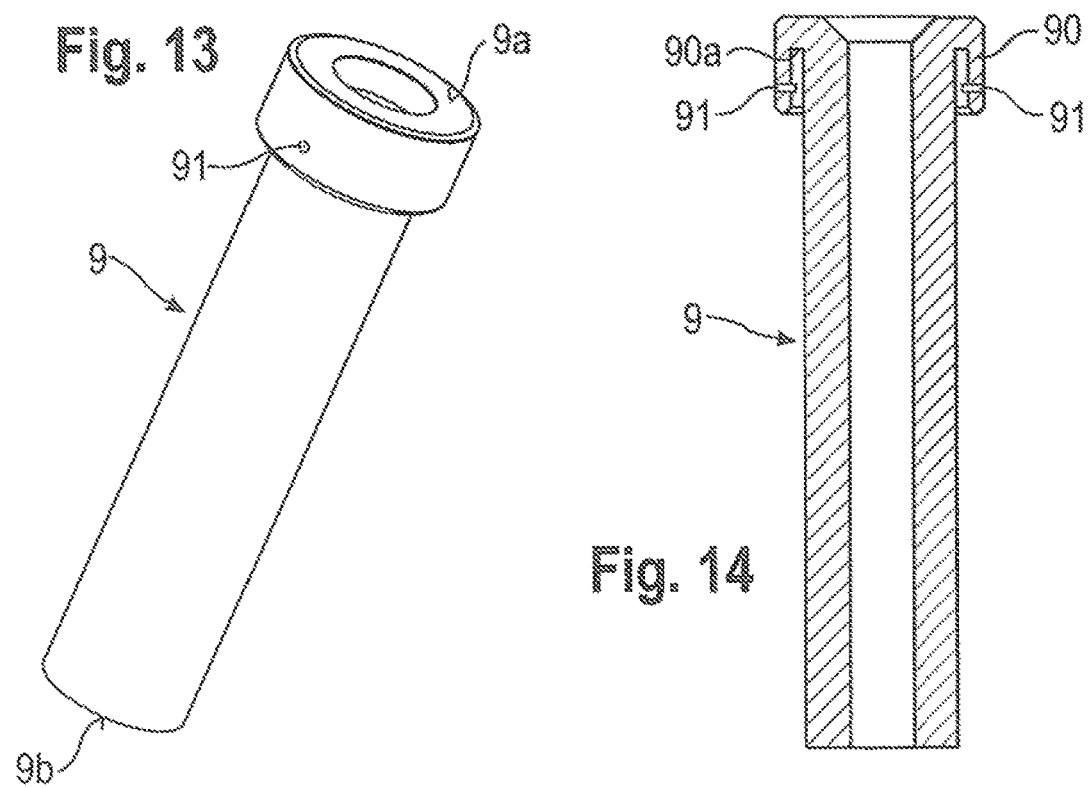

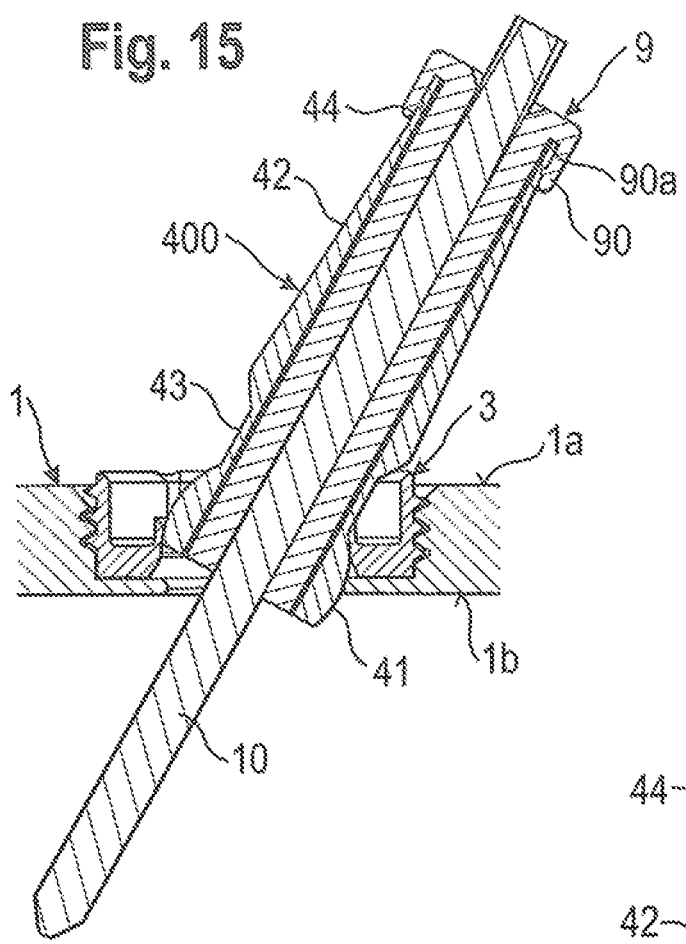
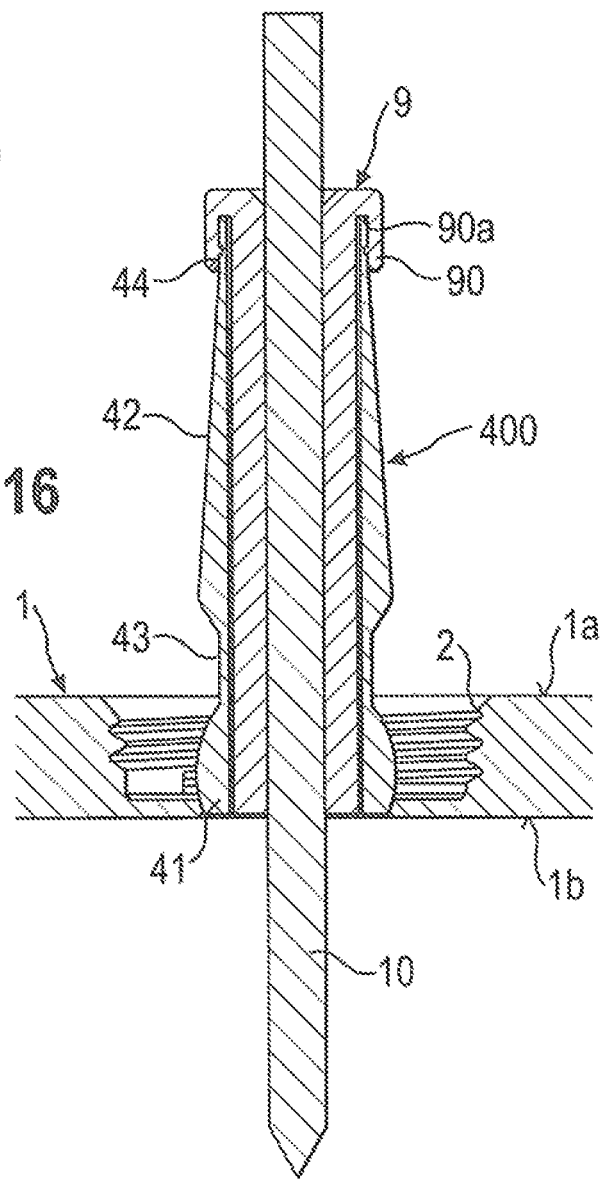

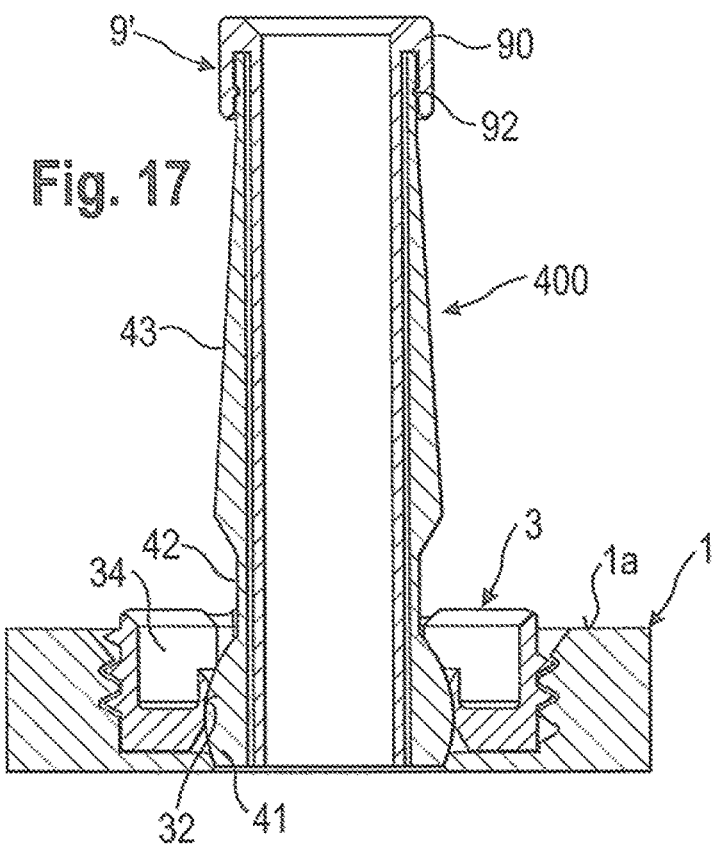
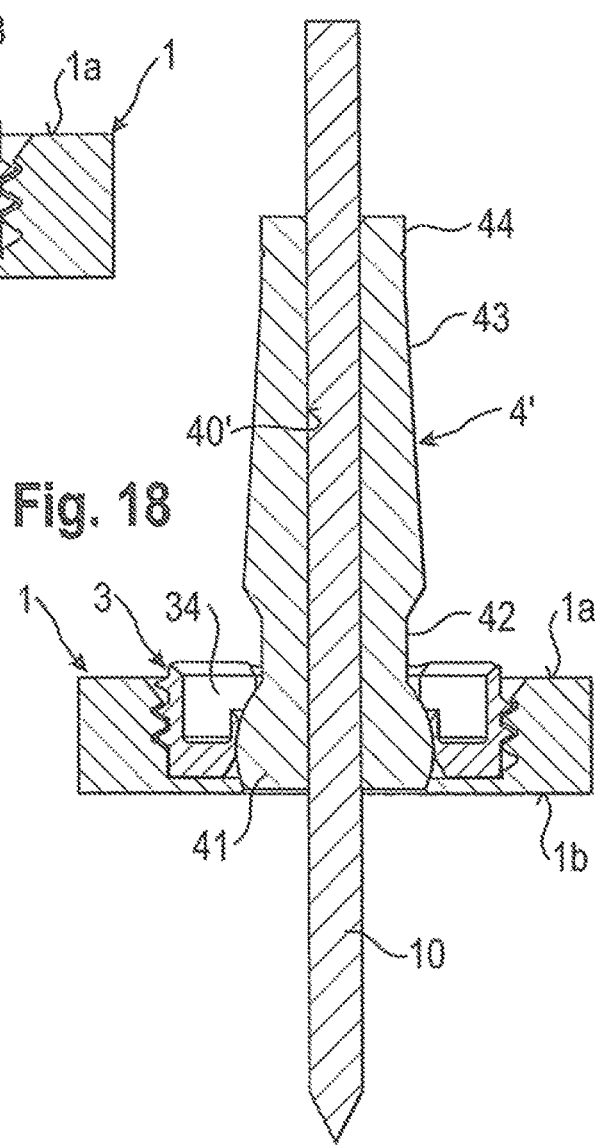

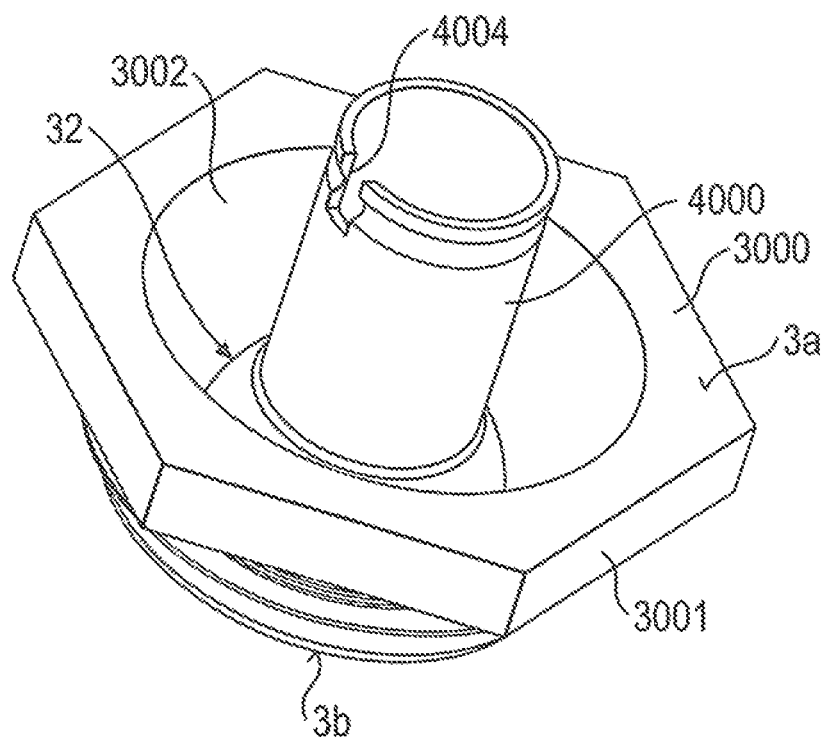

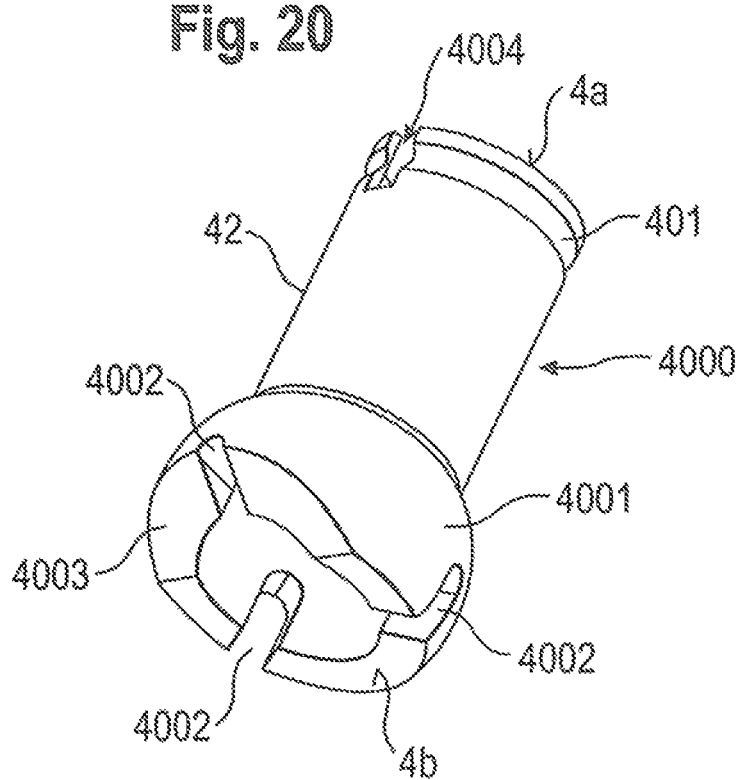

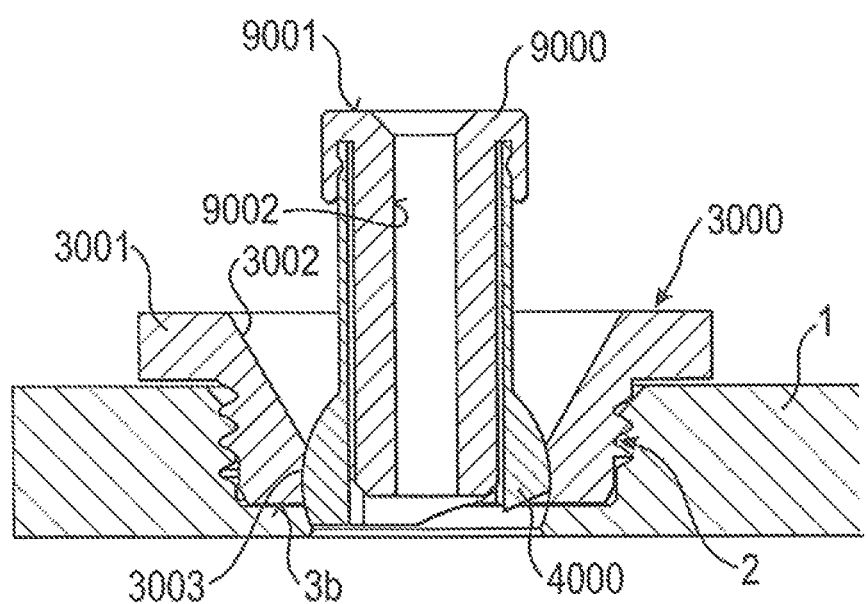

Fig. 22
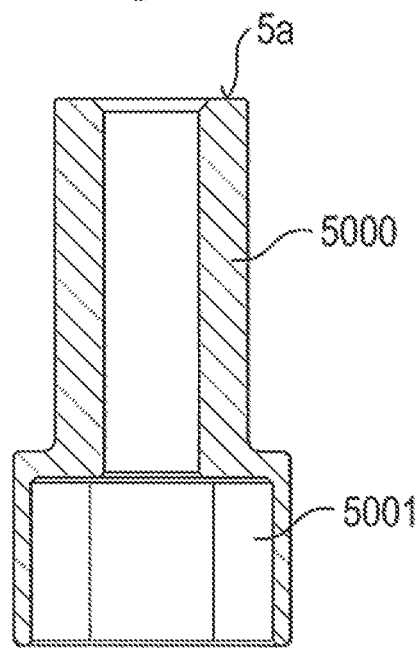
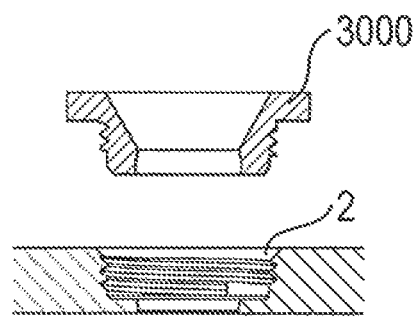

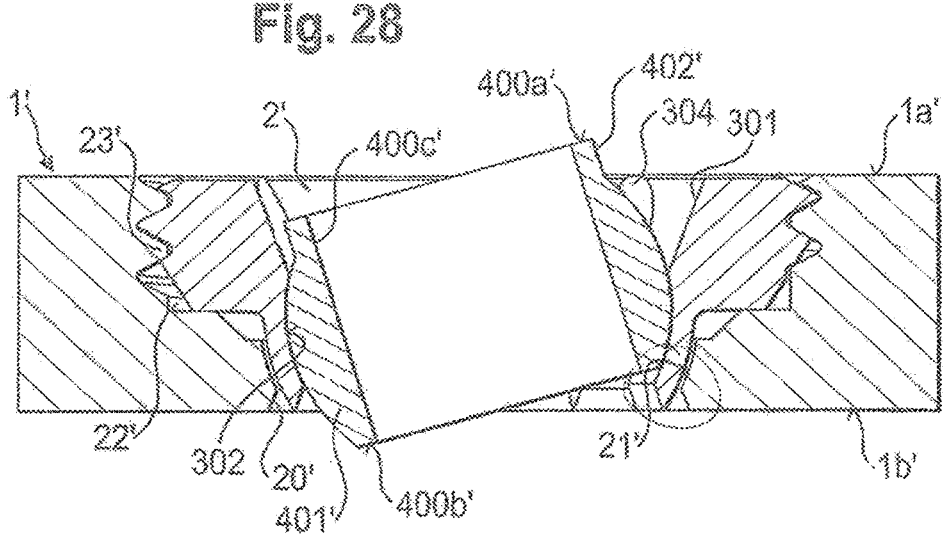
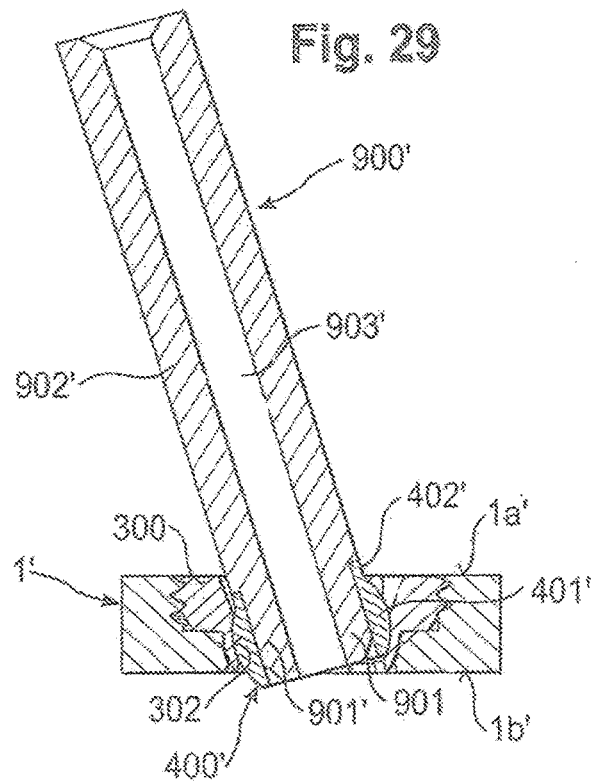

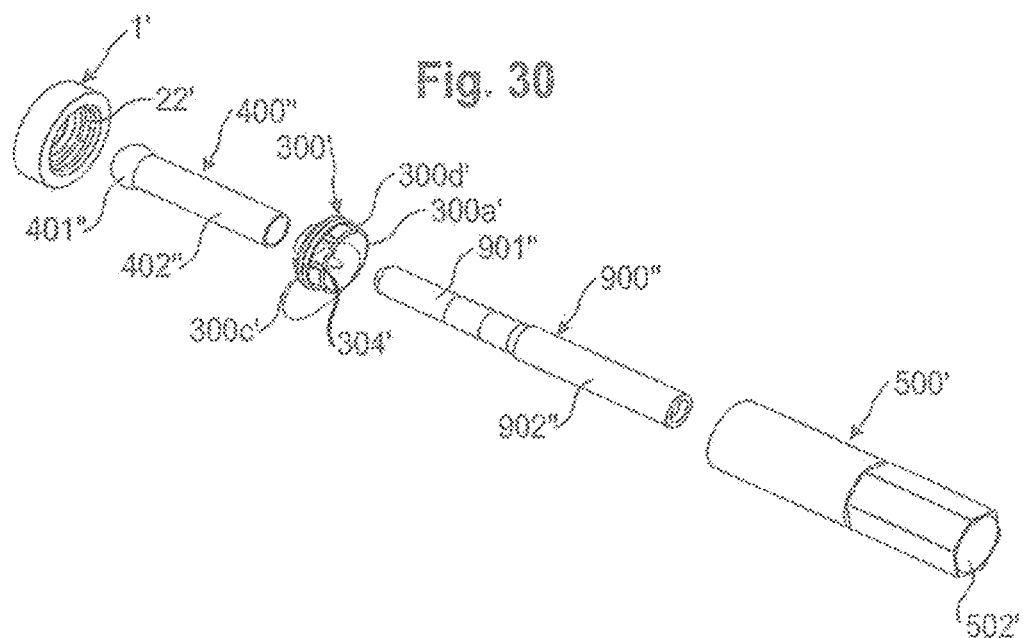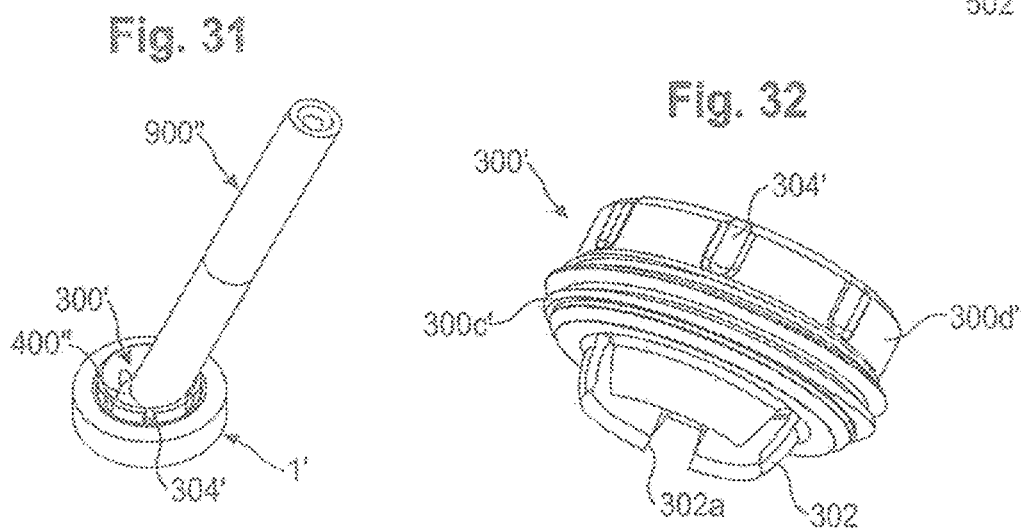

BONE PLATE ASSEMBLY WITH GUIDE MEMBER

CROSS-REFERENCE TO RELATED APPLICATIONS

This application claims priority to and wholly incorporates by reference U.S. provisional patent application No. 61/390,869 with a filing date of Oct. 7, 2010 and European patent application no. 11 159 670.6 with a filing date of Mar. 24, 2011.

FIELD

The invention relates to a bone plate assembly used for the immobilization of bones or bone fragments or vertebrae. The bone plate assembly includes a guide member which provides guidance for a drill bit, a guide wire or an instrument which is used for the correct placement of the bone plate. In particular, the invention relates to a bone plate assembly with a polyaxial coupling between the guide member and the plate.

BACKGROUND

US 2006/0149250 A1 describes a bone plate having a plurality of threaded holes for receiving bone screws, said threaded holes having respective axes, which can be inclined, and a plurality of removable drill guide tips assembled in said threaded holes in alignment with said axes.

EP 1 878 394 A2 describes an orthopaedic fixation plate system comprising a fixation plate include a hole with a spherically-curved inner surface and a polyaxial bushing provided in the hole. A removable guide is provided in the polyaxial bushing. The polyaxial bushings permit the surgeon to modify the angle of each guide and bushing to a selected orientation before locking the bushing at an orientation by tightening the guide into the bushing.

As generally known, after the bone plate is on the bone and one bone anchor is inserted, it is difficult to align the remaining bone anchors to fit into the bone plate ball seat once the bone anchors are fully tightened. However, it is necessary that those bone anchors are placed exactly in the position so that once the bone anchors are tightened, the ball-shaped portion of the bone anchors lines up exactly with the ball-shaped seat in the plate. Misalignment of the ball-shaped portion of the bone anchors and the ball-shaped seat in the plate will cause stresses in the bone and it will prohibit the correct function of the plate.

It is therefore an object of the invention to provide a bone plate assembly with a guide member which is suitable for use with bone screws which are coupled polyaxially to the bone plate and which is simple and versatile in use.

This object, as well as further developments, may be solved by a bone plate assembly according to the embodiments described herein.

SUMMARY

The guide member is held by an insert which can be removably inserted into the hole in the bone plate which is provided to receive the bone screw and a locking member for locking the bone screw in the hole. The insert can be fixed in the hole in the same manner as the locking member of the bone screw. This allows the surgeon to easily place the insert into the hole and then use the guide member for drilling the hole for the bone screw into the bone.

The polyaxial coupling between the insert and the guide member and the guidance for the drill in the center of the hole allows to precisely define the direction of the drill bit for drilling the holes in the bone. Thus, the guide member guarantees that by using a guide wire, a drill, etc., the trajectory of it is perfectly aligned with the ball-shaped seat. This provides a secure and accurate bone anchor placement to assure the proper function of the plate. Further, the locking mechanism for the bone screw and also the bone is protected if the surgeon accidentally slips while using the drill.

The bone plate assembly can be provided as a modular system with various kinds of guide members, such as a guide member for a drill bit, a guide member for a K-wire or a guide member which allows to introduce other instruments, such as syringes for bone cement etc.

Furthermore, the guide member can be provided with a removable bushing which reduces the diameter of the guide channel so that the guide member without the bushing can be used for guiding a drill bit and the guide member with the bushing can be used a guiding a guide wire, for example. Thereby, the versatility of the assembly is increased.

The insert with the guide member can be easily removed after the hole has been drilled into the bone, the bone screw can be inserted and the locking member be tightened.

Further features and advantages of the invention will become apparent from the description of embodiments with reference to the accompanying drawings. In the drawings:

BRIEF DESCRIPTION

FIG. 1 shows a perspective view of the bone plate assembly with guide members.

FIG. 2. shows a schematic sectional view of a hole provided in the plate member of the bone plate assembly of FIG. 1.

FIG. 3 shows a perspective view from the top of an insert provided in the hole of the plate member.

FIG. 4 shows a perspective side view of a guide member provided in the plate member of FIG. 1.

FIG. 5 shows a perspective side view of a tool for inserting the insert shown in FIG. 3 into the hole shown in FIG. 2.

FIG. 6 shows a schematic sectional view along a plane comprising the center axis of the insert of FIG. 3.

FIG. 7 shows a schematic sectional exploded view of the tool, the insert, the guide member and the hole.

FIG. 11 shows a second embodiment of the guide member in a perspective view.

FIG. 12 shows a schematic sectional view of the guide member of FIG. 11, the section being taken in a plane containing the center axis of the guide member.

FIG. 13 shows a perspective view of a bushing to be connected to the guide member of FIG. 11.

FIG. 14 shows a schematic sectional view of the bushing of FIG. 13, the section being taken in a plane containing the center axis.

FIG. 15 shows a schematic sectional view of the plate member with insert and guide member provided with the bushing of FIGS. 13 and 14 and a guide wire guided through the guide member.

FIG. 16 shows a schematic sectional view of the bone plate with the hole and the guide member with bushing and a guide wire already inserted into the bone and the insert removed.

FIG. 17 shows a schematic sectional view of the bone with the bone plate member, the insert, the guide member and a bushing with a larger inner diameter compared to the bushing shown in FIGS. 13 to 16.

FIG. 18 shows a schematic sectional view of the plate member with insert and guide member with a smaller inner diameter compared to the guide member of the other embodiments to accommodate a guide wire.

FIG. 19 shows a perspective view of a subassembly of a third embodiment of the guide member and the insert.

FIG. 20 shows a perspective view of the third embodiment of the guide member.

FIG. 21 shows a schematic sectional view of the plate member and the insert with the guide member of the third embodiment and the bushing, in a perpendicular position.

FIG. 22 shows a sectional side view of a tool for inserting the insert into the hole.

FIG. 28 shows a schematic cross-sectional view of the bone plate assembly of FIG. 26, the section taken in a plane containing the central axis of a hole of the plate member.

FIG. 29 shows a schematic cross-sectional view of the bone plate assembly in the assembled state according to FIG. 27 with the K-wire sleeve.

FIG. 30 shows a perspective exploded view of another embodiment of the bone plate assembly.

FIG. 31 shows the bone plate assembly of FIG. 30 in an assembled state.

FIG. 32 shows a perspective view from the top of an insert of the bone plate assembly according to FIG. 30.

DETAILED DESCRIPTION

Figure 8:
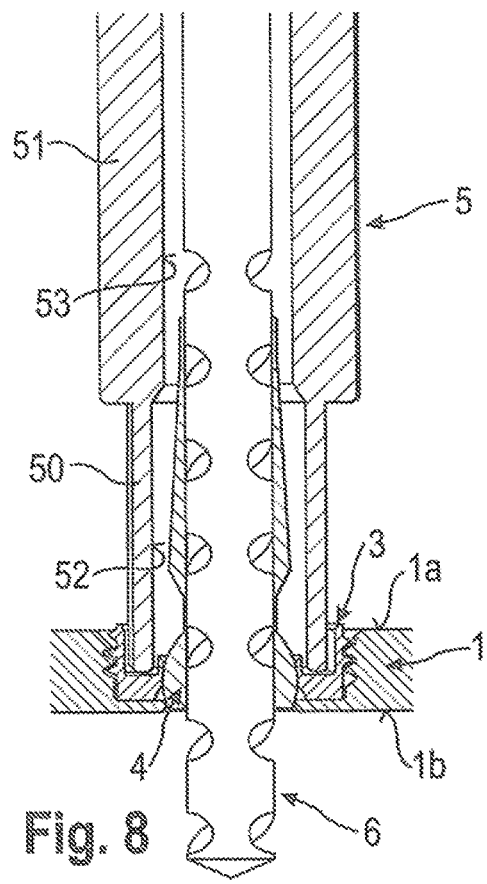
FIG. 8 shows a schematic sectional view of the plate member with the insert and the guide member and the tool of FIGS. 1 to 7 with a drill bit guided through the guide member.

A first embodiment of the bone plate assembly will now be described with reference to FIGS. 1 to 9. As shown in FIG. 1, the bone plate assembly includes a plate member 1 which is in this embodiment a substantially elongate body with a top side 1a and a bottom side 1b. A plurality of holes extend through the plate member from top side 1a to the bottom side 1b. The number and arrangement of the holes can vary according to the size and the shape of the plate member 1. The holes 2 are intended for receiving bone anchors, for example bone screws to fix the plate member 1 to a bone surface, for example, to broken bone parts or to vertebrae.

In the holes, as shown in FIG. 1 in each hole, an insert 3 is provided which is removably connectable to the wall of the hole 2. A guide member 4 is received in the insert 3. In the embodiment shown, a plurality of guide members are received in the respective inserts 3. It has to be understood, that the number of inserts 3 with guide members 4 which are provided in the plate member with the holes 2 can vary according to the actual requirements for the bone plate assembly.

As shown in FIG. 2, the hole 2 comprises an opening 20 towards the bottom side 1b and adjacent the opening 20 a hollow seat portion 21 to receive the head of a bone screw in a pivotable manner. Between the seat portion 21 and the top side 1a a cylindrical bore 22 with an internally threaded portion 23 is provided. The inner diameter of the bore 22 is larger than the inner diameter of the seat portion 21. The threaded portion 23 can have any thread form, for example a metric thread. The thread can also be a two-start thread to allow the plate member to be designed with small thickness.

As shown in particular in FIGS. 1 and 6, the insert 3 is a substantially cylindrical piece with a top side 3a and a bottom side 3b and an overall height between the top side 3a and the bottom side 3b which is such that when the insert is inserted into the bore 22 of the hole 2 its top side 3a is substantially flush with the top side 1a of the plate member 1. The insert 3 has an outer threaded surface portion 30 which cooperates with the threaded portion 23 of the hole 2. The insert 3 further includes a non-threaded outer surface portion 31 extending from the threaded outer surface portion 30 to the top side 3a of the insert 3 and having a greatest outer width that is not greater than an outer width of the insert 3 defined by a thread root 30a of the threaded outer surface portion 30. In the center, the insert 3 has a coaxial through hole 31 which widens into a spherical segment-shaped portion 32 in the direction to the bottom side 3b. The spherical-segment shaped portion 32 continues into a conically widening portion 33 up to the bottom side 3b.

In the top side 3a of the insert a recess 34 for engagement with a tool 5, as shown in FIG. 5, is provided. The recess 34 in the depicted embodiment has an outer hexagon-shaped contour. However, any other recess which allows engagement with a tool is conceivable, for example, any other polygon-shaped recess or star-shaped recess, etc. The inner contour of the recess is substantially cylindrical and the inner wall of the recess has been cut so that an annular rim 35 the height of which is substantially smaller than the outer wall of the recess, remains.

Figure 9:
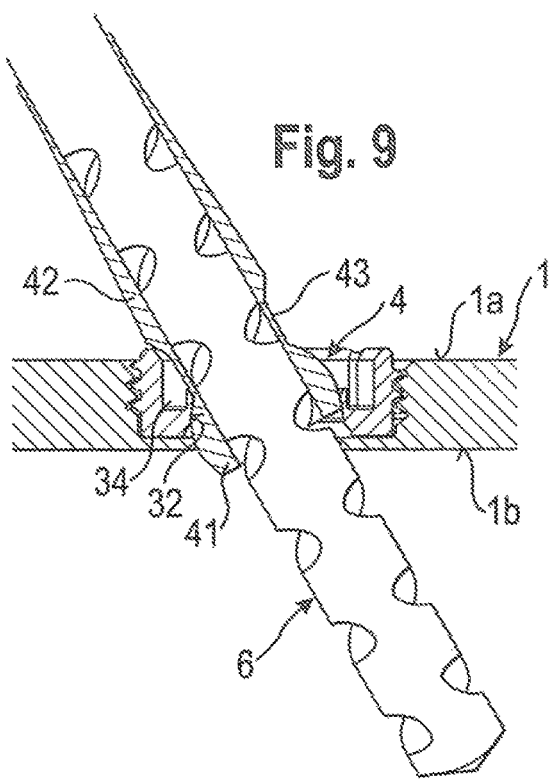
FIG. 9 shows a schematic sectional view of the plate member with the hole and the insert with the guide member and the drill bit guided through the guide member in a pivoted position.

As shown in particular in FIGS. 4 and 7, the guide member 4 is formed as a substantially rotationally symmetric piece with a top end 4a and a bottom end 4b and a guide channel 40 extending from the top end a to the bottom end 4b. In the first embodiment, the guide channel 40 has a diameter which is configured to allow a drill bit 6 as shown in FIGS. 8 and 9 to pass therethrough. The guide member 4 includes a portion 41 with a spherically-shaped outer surface which is oriented such that the diameter increases towards the second end 4b. The guide member further has a shaft portion 42 which extends out of the plate member 1 when the guide member 4 is inserted into the hole 2 and which can serve for gripping and orienting the guide member. The shaft portion 42 has a substantially conically tapering outer surface which tapers towards the top end 4a with a small cone angle. It has to be understood that the conical outer surface is only exemplary and that also another design of the outer surface of the shaft portion 42, such as a cylindrical or polygon-shaped design, is conceivable. The largest outer diameter of the shaft portion 42 is smaller than the largest outer diameter of the spherically-shaped portion 41. Between the shaft portion 42 and the spherically-shaped portion 41 a neck portion 43 with a reduced diameter compared to the outer diameter of the shaft portion 42 and the spherically-shaped portion 41 is provided. The transition of the neck portion 43 to the shaft portion 42 and/or the spherically-shaped portion 41 may be gradual or abrupt. Adjacent the top end 4a, a cylindrical portion 44 may be provided.

The size of the guide member 4 and of the insert 3 is such that the guide member 4 can be introduced from the bottom side 3b into the insert 3, as can be seen in particular in FIG. 7. The shaft portion 42 is passed through the through hole 31 until the spherically-shaped portion 41 of the guide member 4 rests against the spherical-segment shaped portion 32 of the through hole. As can be seen in FIGS. 8 and 9, the spherically-shaped portion 41 of the guide member 4 can extend partly through the through hole 31 so that the spherically-shaped portion 41 can be slightly clamped within the insert 3. The guide member 4 is able to pivot within the insert 3. The neck portion 43 with the reduced diameter encounters a space provided by the recess 34 in the insert which allows pivoting of the guide member 4 with a great range of motion of up to 60°.

The tool 5 which can be used for inserting the insert 3 into the hole 2 is shown in FIG. 5. It comprises a top end 5a and a bottom end 5b, an engagement portion 50 at the bottom end 5b and an upper portion 51 which may serve as a handle. The engagement portion 50 comprises a coaxial bore 52 the diameter of which is larger than the outer diameter of the rim 35 of the insert 3. The outer wall of the engagement portion 50 is adapted to the contour of the recess 34 of the insert, in the embodiment shown, it is a hexagon shape. The upper portion 51 comprises a through bore 53 which allows a drill bit or an other instrument to pass therethrough.

The elements of the bone plate assembly are made of a body compatible material, such as a body compatible metal, for example stainless steel or titanium or a body compatible metal alloy, such as Ni—Ti-alloys for example Nitinol, or of a body compatible plastic material, for example medical grade PEEK or of combinations thereof. For example, the plate member, the inserts and the guide members can be made of the same or of different materials.

The use of the bone plate assembly with the guide member will now be explained with reference to FIGS. 7 to 10. First, the guide member 4 is introduced from the bottom side 3b into the insert 3 until it rests with the spherically-shaped portion 41 in the spherically-shaped portion 32 of the insert. Then, the insert with the guide member 4 therein is screwed by means of the tool 5 into a hole 2. When the insert 3 is fixed in the hole 2 a slight pressure is exerted by the insert and the plate member onto the guide member 4 so that the guide member 4 is slightly clamped in the insert. If the hole which has to be prepared in the bone is a hole which is perpendicular to the plate member 1, the guide member is held in a straight position as shown in FIG. 8. In this case, the tool may remain engaged with the insert 3 and the drill bit 6 can be inserted and passes through the tool 5 and the guide member 4. The tool 5 can be used as a support to keep the drill bit 6 straight.

If an inclined hole has to be prepared in the bone, the tool 5 is removed and the guide member 4 is pivoted until the desired angular position is obtained. Then, as shown in FIG. 9, the drill bit 6 is passed through the guide channel of the guide member 4 and the hole is drilled.

After the hole has been drilled, the drill bit is removed from the hole and the tool 5 is used to screw out the insert. Because of the design of the tool 5 the guide member 4 is pivoted back to the straight position with respect to the plate member which allows to remove the insert with guide member.

Figure 10:
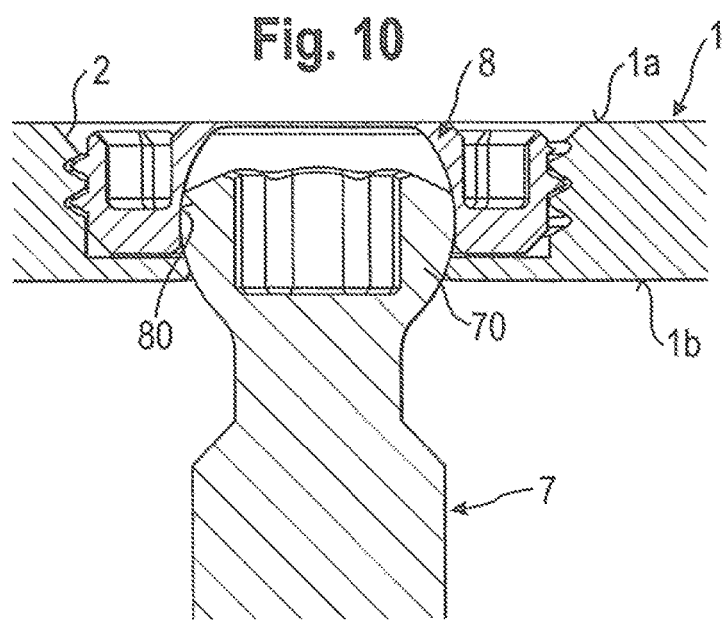
FIG. 10 shows a schematic sectional view of the bone plate member with inserted bone screw and locking element.

Thereafter, as shown in FIG. 10, a bone screw 7 with a spherically-shaped head 70 is inserted into the hole 2 in the plate member and screwed into the prepared hole in the bone. A locking member 8 is thereafter screwed into the hole 2 which presses onto the head 70 within spherically recessed portion 80 to lock the head 70 in the hole 2.

A second embodiment of the guide member will now be explained with reference to FIGS. 11 to 16. Parts or portions which are identical or similar to that of the first embodiment are designated with the same reference numerals and the description thereof will not be repeated. The guide member 400 differs from the guide member 4 in that it has a circular groove 401 at a distance from the top end 4a. The groove is provided in the cylindrical portion 44 and serves for engagement with a fixation element of a bushing 9 which is shown in FIG. 13. The bushing 9 is a cylindrical tube with a top end 9a and a bottom end 9b, wherein an outer diameter of the cylinder is slightly smaller than the inner diameter of the guide channel 40 as shown in FIG. 12 so that the bushing 9 can be introduced into the guide member 400. The inner diameter of the bushing 9 is such that it allows a guide wire, for example, a K-wire 10 to be guided therethrough, as shown in FIGS. 15 and 16. The bushing 9 has at its top end 9a a collar 90. The collar 90 is connected to the bushing and extends, when the bushing 9 is inserted into the guide member 400 at a distance from the outer surface of the guide member along the cylindrical portion 44 of the guide member 400. The connection portion 90a of the collar 90 with a main body of the bushing 9 forms a stop for the insertion of the bushing into the guide member 400.

The bushing 9 is fixed by means of engagement elements 91, which are in this embodiment pins 91 extending through the collar 90 and engaging groove 401. Many possibilities are conceivable for removably fixing the bushing to the guide member. For example, the guide member and the bushing can be held together by a projection and recess made by crimping or by resilient tongues instead of the collar which snap over the guide member. Also, it is conceivable that the bushing has screw thread at the inner side of the collar 90 which engages a corresponding thread on the guide member.

In use, the bushing is inserted into the guide member, which can be done even with the guide member 400 already inserted in the insert 3 which is served into the hole 2. Thereafter, a guide wire is passed through the guide member 400 and the guide member 400 is pivoted into the desired position. Since the bushing 9 is temporarily fixed on the guide member, it cannot fall out. With the guide wire, for example, first the bone fragment can be fixed. If necessary, the guide wire can be introduced into the bone in an inclined orientation, as shown in FIG. 15.

Then, the insert 3 can be removed while the guide wire remains in the bone. This is shown in FIG. 16 for the perpendicular position with respect to the bone plate surface. In the state as shown in FIG. 16, the hole in the bone can be drilled with a cannulated drill. Then, the guide member 400 can be removed and a cannulated screw can be inserted which follows the guide wire. Finally, the guide wire is removed and the locking element 8 as shown in FIG. 10 is screwed into the hole 2 to lock the bone screw.

FIG. 17 shows a further modification of the second embodiment. It differs from the previously described embodiment only in that the inner diameter of the bushing 9' is larger than that of the bushing 9 of the previous embodiment. Also, instead of the pins 91 noses 92 are provided, which can snap in corresponding engagement portions of the outer surface of the bushing 9' which can be groove-shaped or can have another shape. Several bushings with different inner diameter can be provided to allow to adapt the diameter of the guide channel 40 to a specific instrument or drill.

A further modification of the previous embodiments is shown in FIG. 18. The guide member 400' has a guide channel 40' the diameter of which is smaller than the diameter of the guide channel 40 of the previous embodiments and configured to allow to guide a guide wire 10 therethrough. In this case, it is possible to predefine the desired position of the bone screw with the guide wire 10 using the guide member 4' and then removing the insert 3 with the guide member 4' while the guide wire remains in the bone. Thereafter it is possible to screw a cannulated screw following the guide wire in the bone without pre-drilling a hole.

FIG. 19 shows a possible subassembly of an insert 3000 and a guide member 4000 of a third embodiment, respectively. As described below, the guide member 4000 is detachably attachable to the insert 3000.

The construction of insert 3000 is substantially identical to the construction of the insert of the other embodiments. However, instead of the recess 34 for engagement with the tool 5, the insert 3000 is provided with a hexagon 3001 at its circumference, which is adapted to fit in a tool described hereinafter. Instead of the recess 34 having a hexagon socket, the insert 3000 is provided with a tapered recess 3002 or the like to provide space for the pivoting of the guide member. The hexagon socket 34 of the recess for engagement with the tool of the previously described insert 3 is replaced by hexagon 3001 at the circumference of the insert 3000. It should be noted that instead of a hexagon another outer engagement structure such as for example another polygon structure can be used.

Also, the construction of the guide member 4000, shown in FIG. 20, is substantially identical to the construction of the guide members of the other embodiments and identical reference signs are used, if suitable. However, the guide member 4000 has a spherical-segment shaped first portion 4001 which is provided with slots 4002 which extend from the bottom end 4b in a direction toward the shaft portion 42. In this direction, the slots are formed until about the center of the sphere of the spherical-segment shaped first portion 4001. The provision of these slots 4002 renders the spherical-segment first portion 4001 flexible to some extent when radial forces act on the spherical-segment first portion 4001 in the lower region.

Further, the spherical-segment first portion 4001 is provided with an angled flat portion 4003. The angled flat portion 4003 extends from the bottom end 4b into the outer surface of the spherical-segment first portion 4001. The angle between the bottom end 4b and the angled flat portion 4003 portion is about 30°. In alternative embodiments, the angle may differ dependent on the surrounding construction. The angled flat portion 4003 serves for avoiding contact between the guide member 4000 and the bone when the guide member 4000 is tilted even when the plate member 1 is in full contact with the underlying bone. If a contact between the bone and the guide member occurs, there might be a risk of bone necrosis. Due to this design, a gap of about 1 mm between the guide member 4000 and the bone is possible.

At the top end 4a, the guide member 4000 is provided with an identification notch 4004. The identification notch 4004 extends from the top end 4a in a direction toward the spherical-segment first portion 4001. The identification notch 4004 is aligned with the angled flat portion 4003 at the bottom end 4b of the guide member 4000. Therefore, it is possible to know the axial orientation of the guide member 4000 and the location of the angled flat portion 4003 even when the angled flat portion 4003 can not be seen because the guide member is mounted in the hole 2 of the plate and it is possible to rotate the guide member 4000 such that a desired orientation of a tilt angle without contacting the bone may be adjusted. The function of the identification notch may be constructed in an alternative way and at a different location if it is possible to recognize the orientation of the angled flat portion 4003. Other types of identification marks can be used such as printed marks or elevated marks.

As to be seen in FIG. 21, the insert 3000 is provided with a spherical-shaped segment portion 3003 below the tapered recess 3002 in a direction toward the bottom side 3b. The spherical-shaped segment portion 3003 has an increased ball contact area which slightly extends, in the direction toward the bottom side 3b, beyond the center of the sphere of the spherical-shaped segment portion 3003.

Therefore, there is a form fit connection between the spherical-shaped segment portion 3003 and the spherical-shaped first portion 4001 of the guide member 4000. However, due to the elastic characteristic of the spherical-shaped first portion 4001 because of the slots 4002, it is possible to removably attach the spherical-shaped first portion 4001 to the spherical-shaped segment portion 3003 by clicking the spherical-shaped first portion 4001 into the spherical-shaped segment portion 3003.

Differently from the preceding embodiments in which the spherical-shaped first portion of the guide members is clamped between the insert 3 and the seat portion 21 of the plate member 1, the spherical-shaped first portion 4001 of the guide member 4000 is merely held by the form fit connection and the friction force between the spherical-shaped segment portion 3003 and the spherical-shaped first portion 4001. When the insert is tightened, the bottom side 3b of the insert abuts against the bottom of the hole 2 without changing the clamping force between the spherical-shaped segment portion 3003 and the spherical-shaped first portion 4001. Therefore, even if the insert 3000 is strongly tightened, it will be possible to tilt the guide member 4000 and the clamping force does not depend on the tightening torque.

Further, in FIG. 21 it is to be seen, that the hexagon 3001 is located outside the plate member 1 to enable the tool to engage with the hexagon 3001.

A bushing 9000 is snapped onto the guide member 4000 similar to the bushing 90 snapped on the guide member 400. However, alternatively, the bushing also can be attached in a different way. The bushing 9000 is provided with a channel 9002 having a slightly tapered shape. The smaller diameter of the channel 9002 is located at the top end 9001 of the bushing 9000. The smaller inner diameter of the bushing 9 is such that it allows a guide wire, for example, a K-wire to be guided therethrough. However, if obstacles exist in the channel having a constant inner diameter, the guide wire may be clamped in the channel, which is avoided in this embodiment due to the tapered shape of the channel.

FIG. 22 shows the tool 5000 for inserting the insert 3000 into the hole 2. The tool 5000 comprises a recess 5001 having a cross section adapted to the hexagon 3001 of the insert 3000. The depth of the recess 5001 in a direction toward the top end 5a is larger that the height of the hexagon

3001. Further, the depth of the recess 5001 is adapted to accommodate the insert 3000 and the guide member 4000 even if the guide member 4000 is in any tilted or straight position within its full range of motion. Therefore, it is possible to use the tool 5000 for inserting or removing the insert 3000 independent of the angular position of the guide member 4000.

In use, first, the guide member 4000 is clicked into the insert 3000, forming a subassembly as shown in FIG. 19. Then, as with the other embodiments, the insert 3000 with the guide member 4000 therein is screwed into the hole 2 by means of the tool 5000. The guide member 4000 is clamped by the friction force such that its tilting angle can be adjusted in advance. The tilted or straight guide member 4000 can be held in a preset angular position because, due to its depth, the recess 5001 of the tool is able to accommodate the insert 3000 and the guide member 4000 in any of the tilted or straight positions within the full range of the motion of the guide member 4000.

Then, the tool 5000 is removed and, if desired, the tilting angle of the guide member 4000 is adjusted. Subsequently, the drill bit is passed through the guide channel of the guide member 4000 and the hole is drilled.

After the hole has been drilled, the drill bit is removed from the hole and the tool 5000 is used to screw out the insert. Because of the design of the tool 5000, the guide member 4000 has not to be pivoted back to a straight position so that it is possible to remove the guide member 4000 even if a guide wire stays in the bone in case that the use of a cannulated screw or other device is needed.

There further use is comparable with the bone plate assembly of the other embodiments.

By providing different guide members with different inner diameters and different kinds of bushings a modular system can be obtained which allows the surgeon to apply it in a great variety of procedures.

Figure 23:
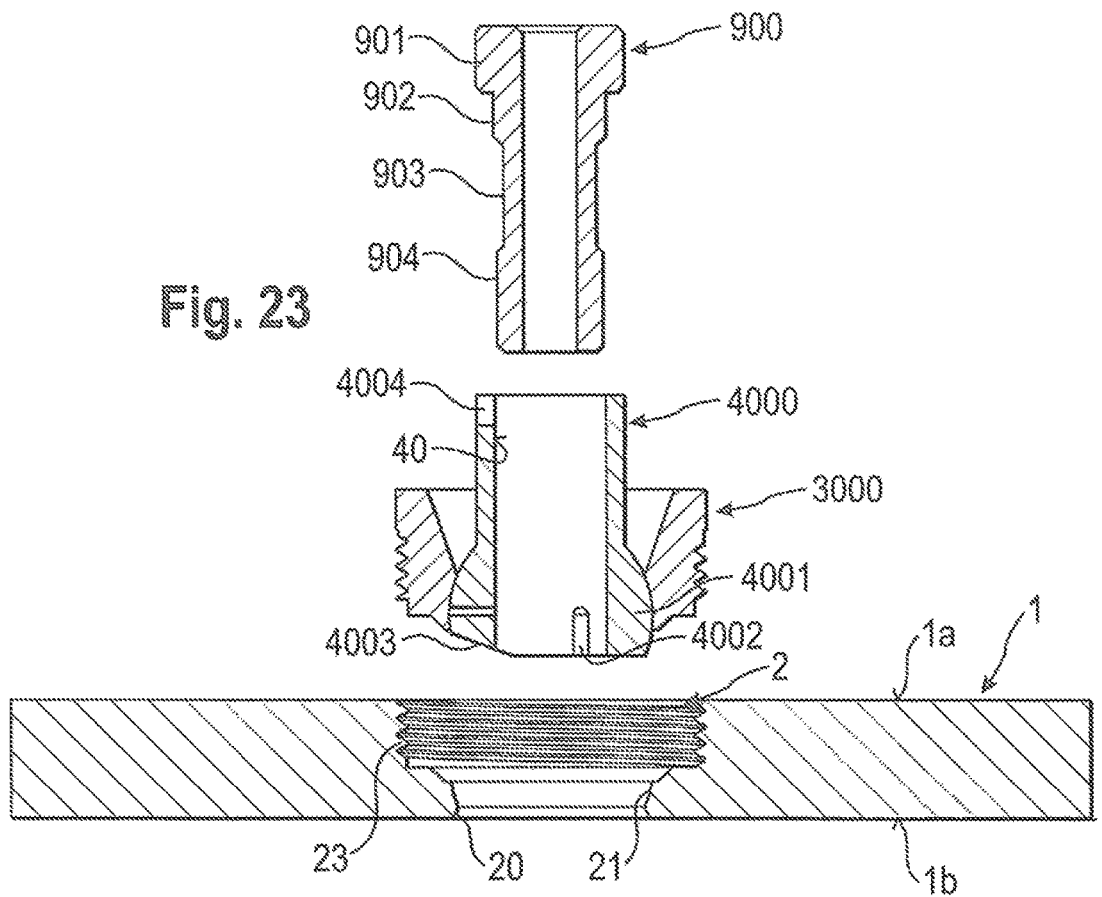
FIG. 23 shows a schematic exploded sectional view of a bone plate with insert, guide member and a further modified bushing.
Figure 24:
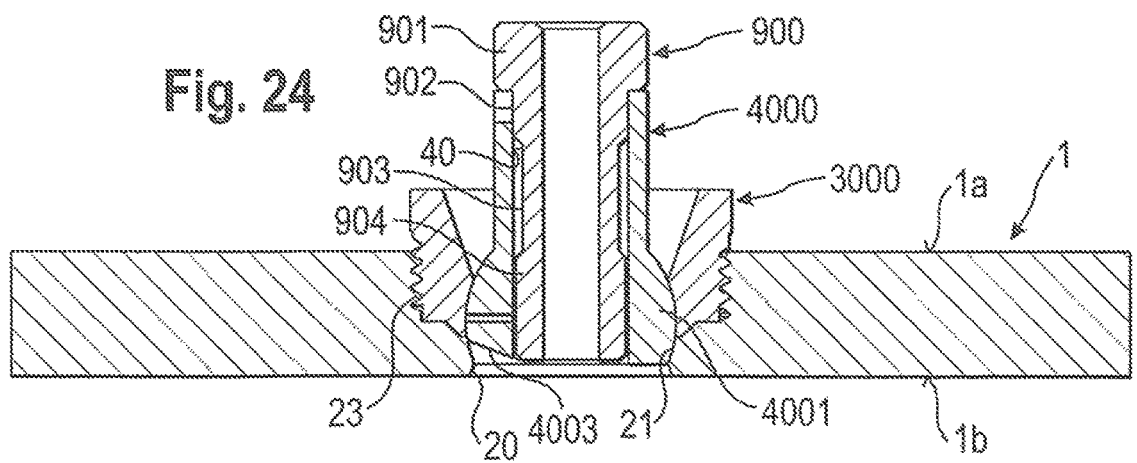
FIG. 24 shows a schematic sectional view of the assembly of FIG. 23 in a mounted state.
Figure 25:
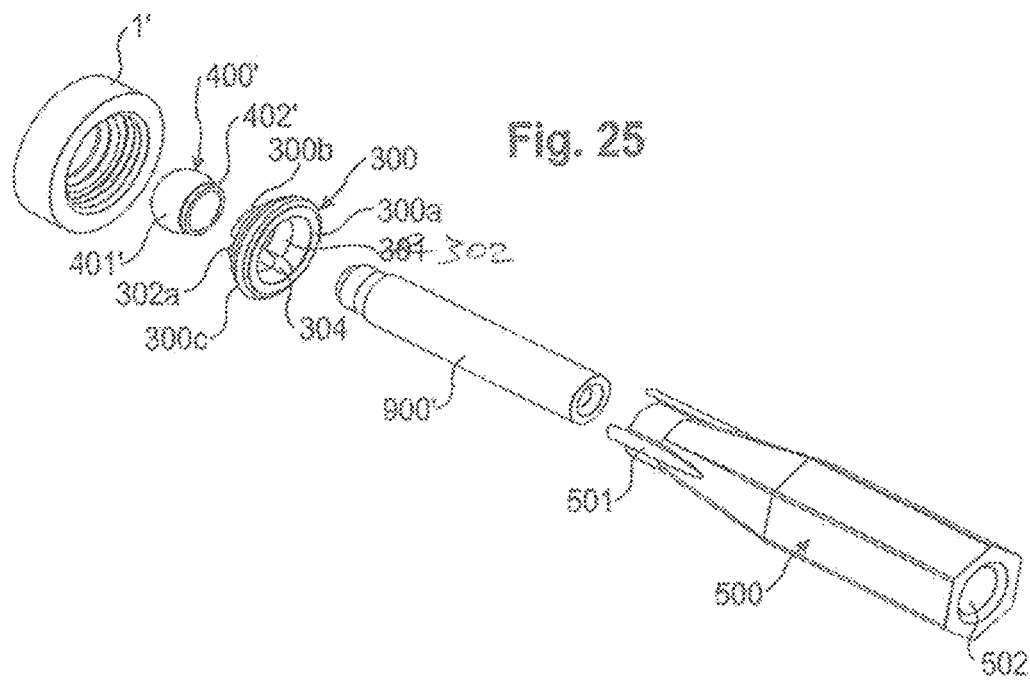
FIG. 25 shows a perspective exploded view of a further embodiment of the bone plate assembly.
Figure 26:
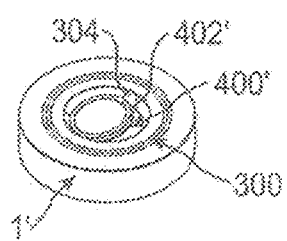
FIG. 26 shows a perspective view of the bone plate assembly of FIG. 25 without a K-wire sleeve.
Figure 27:
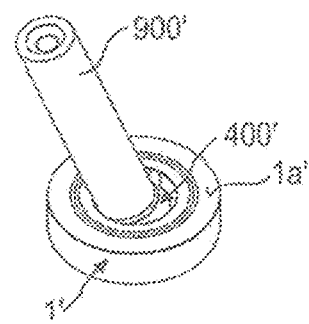
FIG. 27 shows a perspective view of the bone plate assembly of FIG. 25 in an assembled state with the K-wire sleeve.

A further modified bushing 900 is shown in FIGS. 23 and 24 together with the guide member 4000 and the insert 3000 of the third embodiment. However, it should be noted that the bushing 900 can be used with any other guide member and insert of the other embodiments described. The bushing 900 has a first portion 901 with an outer diameter that is greater than the inner diameter of the guide channel 40. The first portion is followed by a second portion 902 with an outer diameter that is sized such that the bushing is held by friction within the guide channel 40. A third portion 903 may follow with an outer diameter that is smaller than the inner diameter of the guide channel and a fourth portion 904 with an outer diameter that is slightly smaller than the inner diameter of the guide channel 40. The number of portions can vary. However the upper thickened first portion provides a stop for limiting the insertion of the bushing. The inner diameter of the bushing is configured to allow the introduction of a drill bit or is configured to allow the introduction of a guide wire or another instrument.

The bushing 900 is easy to manufacture.

Other modifications and variations of the above described embodiments can be made. For example, the connection between the insert and the plate member can be another releasable connection, such as, for example a bayonet connection. The shape of the guide member can vary. For example, the shaft portion can be longer or shorter as in the embodiment shown.

Generally, the insert can be provided with an engagement portion, for example with a hexagon 3001 for a screwdriver at its circumference.

Generally, the guide member 400, 4000 can be provided with a circumferential groove 40 and the bushing can be snapped into the groove 401.

Generally, the bushing 9000 can be provided with a channel 9002 having a slightly tapered shape the smaller inner diameter of which is located at a top end 9001 of the bushing 9000.

As bone anchor, all kinds of bone anchors as such as bone screws, bone nails etc. can be used.

Referring to FIGS. 25 to 29, a further embodiment of the bone plate assembly is shown. The plate member 1' is shown in a simplified manner as a circular plate member. However, the plate member 1' can have any shape including a shape as shown, for example, in FIG. 1. The plate member 1' has a top side 1a' and a bottom side 1b' and a hole 2' extending from the top side 1a' to the bottom side 1b'. Like in the previous embodiments, the hole 2' comprises an opening 20' towards the bottom side 1b' and adjacent the opening 20' a hollow seat portion 21'. Between the seat portion 21' and the top side 1a' a cylindrical bore 22' with an internally threaded portion 23' is provided. The bore 22' is less deep than the bore 22 of the previous embodiments and the hollow seat portion 21' is larger in axial direction compared to the previous embodiments. The seat portion 21' has a hollow spherical segment shape.

The insert 300 of this embodiment is a substantially rotationally symmetrical piece with a top side 300a and a bottom side 300b and an overall height between the top side 300a and the bottom side 300b such that when the insert 300 is within the hole 2' the top side 300a is substantially flush with the top side 1a' of the plate member 1'. The insert further has an outer threaded surface portion 300c cooperating with the threaded portion 23' of the hole 2'. Adjacent the bottom side 300b, a hollow spherical segment-shaped portion 302 is provided that has a spherical outer surface fitting into the seat portion 21' and a spherically-shaped inner surface portion accommodating a guide member 400' described below. The hollow spherical segment-shaped portion 302 is slotted with at least one, preferably a plurality of slots 302a, extending in axial direction. The slots 302a render hollow spherical segment-shaped portion 302 flexible in radial direction. This facilitates insertion of the guide member 400'.

The insert 300 further comprises a tapered recess 301 and a plurality of engagement portions 304 adjacent the top side 300a. The engagement portions 304 serve for engagement with a tool 500.

The guide member 400' is a substantially rotationally symmetric piece with a top end 400a', a bottom end 400b', a guide channel 400c' extending from the top end to the bottom end. The guide member 400' further has a spherically-shaped outer surface portion 401' adjacent the bottom end 400b' that extends over an axial length including a largest outer diameter of the spherical portion. The spherically-shaped outer surface portion 401' fits into the hollow spherical segment-shaped portion 302 of the insert 300. Adjacent the top end 400a' a cylindrical shaft portion 402' is provided that is shorter than the shaft portion of the previous embodiments and does not project or projects only slightly out of the top side 1a' of the plate member 1'. The guide member 400' has a guide channel 400c' extending from the top end 400a to the bottom end 400b.

A bushing 900' is provided that can be connected to guide member 400'. The bushing 900' comprises a first section 901' with an outer diameter that is slightly smaller than the inner diameter guide channel 400c so that the bushing 900' can be connected in press-fit manner to the guide member 400'.

Adjacent the first portion 901' a second portion 902' is provided with an outer diameter such that when the bushing 900' is connected with the guide member 400', the outer surface of the second portion 902' is flush with shaft portion 402' of the guide member 400'. The bushing 900' has coaxial through channel 903' with diameter sized so as to allow a guide wire, for example a K-wire, to be guided therethrough.

The tool 500 which comprises a front portion having engagement portions 501 for engagement with the engagement portions 304 of the insert 300. The tool 500 also comprises a coaxial through channel 502 the diameter of which is larger than the outer diameter of the bushing 900'.

In use, the guide member 400' may be preassembled with the insert 300 and the bushing 900' and inserted altogether using the tool 500 into the plate member 1'. Once the plate member 1' is placed onto the bone or the bone part or fragment, a K-wire can be guided through the bushing 900' and the guide member 400' into the bone. Then, the insert 300 can be removed together with the guide member 400 and bushing 900' and a hole in bone can be drilled with a cannulated drill. Thereafter, a cannulated screw can be inserted which follows the guide wire. Finally, the guide wire is removed and a locking element as previously described is screwed into the hole 2' to lock the bone screw. The embodiment described is particularly suitable for application in MIS (minimally invasive surgery).

FIGS. 30 to 32 show another embodiment of the bone plate assembly. Parts that are identical to the previous embodiment have the same reference numerals and the description thereof is not repeated. The insert 300' has between the threaded outer surface portion 300c' and the top side 300a' a cylindrical portion 300d' with engagement portions 304' at the outer surface for engagement with a tool 500'. The tool 500' has coaxial through channel 502' with engagement portion at the inner wall of one end that engages the engagement portions 304' of the insert 300'. The guide member 400" has a longer shaft portion 402" compared to the previous embodiment. The bushing 900" has a longer first portion 901" that is inserted in the shaft portion 402". In addition, the bushing 900" comprises a second portion 902" projecting out of the shaft portion 402" of the guide member 400". In an assembled state, as shown in FIG. 31, the shaft portion 402" and the second portion 902" of the bushing project out of the insert 300 and out of the top side 1a' of the plate member 1'.

Use of the bone plate assembly may be similar to the previous embodiment. Because of the long shaft portion 402" of the guide member 400" and of the long second portion 902" of the bushing 900", the bone plate assembly is also useful for MIS applications.

In another embodiment, a bone plate assembly includes a plate member with a top side and a bottom side, at least one hole extending from the top side to the bottom side, an insert arranged in the hole, the insert having a through hole, and a guide member removably arranged in the through hole of the insert, the guide member having a guide channel and an outer surface portion which engages an inner wall portion of the through hole so as to allow a pivoting movement of the guide member within the insert. The insert has a spherically-shaped inner surface portion which cooperates with a spherically-shaped outer surface portion of the guide member.

In still another embodiment, a bone plate assembly includes a plate member with a top side and a bottom side, at least one hole extending from the top side to the bottom side, an insert arranged in the hole, the insert having a through hole, and a guide member removably arranged in the through hole of the insert, the guide member having a guide channel and an outer surface portion which engages an inner wall portion of the through hole so as to allow a pivoting movement of the guide member within the insert. The bone plate assembly is arranged such that when the shaft portion of the guide member passes sufficiently through the through hole of the insert, the guide member rests against the through hole.

In yet another embodiment, a bone plate assembly includes a plate member with a top side and a bottom side, at least one hole extending from the top side to the bottom side, an insert arranged in the hole, the insert having a through hole, and a guide member removably arranged in the through hole of the insert, the guide member having a guide channel and an outer surface portion which engages an inner wall portion of the through hole so as to allow a pivoting movement of the guide member within the insert. The guide member is held by friction within the insert.

Although the invention has been described above with respect to various embodiments, it is limited only by the claims.

The invention claimed is:

1. A bone plate system, comprising:
a plate member with a top side, a bottom side and a first hole and a second hole each extending through the plate member from the top side to the bottom side, each of the first and second holes including an inner wall portion comprising an internal threaded portion, a seat portion between the internal threaded portion and the bottom side, the seat portion having a spherical-segment shape, and a diameter smaller than a smallest diameter of the internal threaded portion;
an insert configured to be arranged in each of the first hole and the second hole, the insert having a top side, a bottom side, a through hole and an inner wall portion defining at least a portion of the through hole of the insert, the insert further including a threaded outer surface portion configured to screw into the internal threaded portion, the threaded outer surface portion having a first end and a second end, wherein when the threaded outer surface portion is fully screwed into the internal threaded portion of the plate member with the second end directed towards the seat portion of the plate member, the top side of the insert is configured to be substantially flush with the top side of the plate member such that an entirety of the insert does not protrude above the top side of the plate member;
a guide member configured to be removably arranged in the through hole of the insert, the guide member comprising a guide channel and a spherical-segment shaped outer surface portion configured to engage the inner wall portion of the insert so as to allow a pivoting movement of the guide member when the guide member is arranged in the through hole of the insert, the guide member further comprising a shaft portion monolithic with and extending away from the spherical-segment shaped outer surface portion, the guide channel extending through the shaft portion;
a bone screw configured to be arranged in the seat portion in each of the first hole and the second hole, the bone screw comprising a head portion having a spherical-segment shape corresponding to the spherical-segment shape of the seat portion to engage the plate member in the seat portion to anchor the plate member to a bone, the spherical-segment shape of the head portion adapted to be substantially located below the top side of the plate member when the head portion of the bone screw is axially arranged in the seat portion; and a locking member configured to screw into the internal threaded portion in each of the first hole and the second hole to lock the bone screw in the seat portion, wherein the insert comprises a tapered recess between the top side of the insert and the inner wall portion, the tapered recess being increasingly larger in a direction toward the top side of the insert to provide space for movement of the shaft portion of the guide member in the tapered recess during the pivoting movement of the guide member when the guide member is arranged in the insert.

2. The bone plate system of claim 1, wherein the shaft portion has a length such that the guide member projects out of the top side of the plate member when the guide member is arranged in the through hole of the insert and the insert is arranged in the first hole of the plate member.

3. The bone plate system of claim 1, wherein the guide channel of the guide member has an inner diameter configured to allow a drill bit to pass through and/or to allow a guide wire or another guiding instrument to pass therethrough.

4. The bone plate system of claim 1, further comprising a bushing removably connectable to the guide member and configured to reduce an internal diameter of the guide channel.

5. The bone plate system of claim 4, wherein the bushing is insertable into the guide channel and has a stop to limit the insertion of the bushing relative to the guide member.

6. The bone plate system of claim 1, wherein the spherical-segment shaped outer surface portion extends continuously from a bottom end of the guide member to the shaft portion along at least one side of the guide member.

7. The bone plate system of claim 1, wherein a portion of the shaft portion is passable through the through hole of the insert such that when the portion of the shaft portion passes through the through hole of the insert, the spherical-segment shaped outer surface portion of the guide member is configured to rest against the inner wall portion of the insert.

8. The bone plate system of claim 1, wherein the guide member is held by friction within the insert.

9. The bone plate system of claim 1, wherein a largest width of the insert is not greater than a largest diameter of the first hole.

10. The bone plate system of claim 1, wherein the tapered recess is configured to extend into the first hole when the guide member is arranged in the through hole of the insert and the insert is arranged in the first hole.

11. The bone plate system of claim 1, wherein when the threaded outer surface portion of the insert is screwed into the internal threaded portion of the plate member with the second end of the insert directed towards the seat portion of the plate member, the first end of the threaded outer surface portion is configured to assume an axial position that is between the top side and the bottom side of the plate member.

12. The bone plate system of claim 1, wherein the insert further comprises a spherical-segment shaped outer surface portion extending from the threaded outer surface portion, the spherical-segment shaped outer surface portion of the insert corresponding in size to the spherical-segment shape of the head portion of the bone screw and to the spherical-segment shape of the seat portion.

13. The bone plate system of claim 1, further comprising a bushing with an inner channel, wherein the bushing is insertable at least partially into the guide channel of the guide member and removably connectable to a free end of the shaft portion of the guide member, such that the inner channel communicates with the guide channel and extends a length of the guide member.

14. The bone plate system of claim 1, wherein a greatest width of an opening defined by the tapered recess at the top side of the insert is smaller than an outer width of the insert defined by a thread root of the threaded outer surface portion.

15. The bone plate system of claim 1, wherein when the guide member is in the through hole of the insert and the insert is in the first hole of the plate member, the guide member is pivotable to a first position where the spherical-segment shaped outer surface portion of the guide member extends axially to the top side of the plate member, and to a second position where the spherical-segment shaped outer surface portion of the guide member extends axially to the bottom side of the plate member.

16. The system of claim 1, wherein:
the insert is assembled in the first hole of the plate and the guide member is inserted into the through hole of the insert, such that the insert is interposed between the guide member and the seat portion of the first hole.

17. The system of claim 1, wherein:
the insert has a hollow spherical-segment shaped portion having at least one slot to permit the spherical-segment shaped portion to flex in a radial direction, and the spherical-segment shaped portion of the insert extends to the bottom side of the plate member, and
when the spherical-segment shaped portion of the insert extends between the outer surface portion of the guide member and the seat portion of the one of the first and second holes of the plate, contact between the spherical-segment shaped outer surface portion of the guide member and the seat portion is prevented.

18. A bone plate system, comprising:
a plate member with a top side, a bottom side and a first hole and a second hole extending through the plate member from the top side to the bottom side, each of the first and second holes including an inner wall portion comprising an internal threaded portion, a seat portion between the internal threaded portion and the bottom side, and a diameter smaller than a smallest diameter of the internal threaded portion;
an insert configured to be arranged in each of the first hole and the second hole, the insert having a top side, a bottom side, a through hole and an inner wall portion defining at least a portion of the through hole of the insert, the insert further including a threaded outer surface portion configured to screw into the internal threaded portion, wherein when the threaded outer surface portion is fully screwed into the internal threaded portion of the plate member with the second end directed towards the seat portion of the plate member, the top side of the insert is configured to be substantially flush with the top side of the plate member such that an entirety of the insert does not protrude above the top side of the plate member,
a guide member configured to be removably arranged in the through hole of the insert, the guide member comprising a guide channel extending through the guide member, a shaft portion and a spherical-segment shaped outer surface portion monolithic with the shaft portion, the outer surface portion extending from a bottom end of the guide member to the shaft portion, the outer surface portion extending continuously from the bottom end of the guide member to the shaft portion along at least one side of the guide member, the outer surface portion configured to engage the inner wall portion of the insert so as to allow a pivoting movement of the guide member when the guide member is arranged at a first position in the through hole of the insert and such that the outer surface portion is configured to be arranged in the seat portion when the guide member is arranged in the through hole of the insert and the insert is arranged in the first hole of the plate member, and wherein a portion of the shaft portion projects out of the top side of the plate member when the guide member is arranged in the through hole of the insert and the insert is arranged in the first hole of the plate member;

a bone screw having a head portion configured to be arranged in the seat portion of each of the first hole and the second hole and engage the plate member in the seat portion of the respective first and second holes to anchor the plate member to a bone, the head portion of the bone screw substantially located below the top side of the plate member when axially arranged in the seat portion; and a locking member configured to screw into the internal threaded portion of each of the first hole and the second hole to lock the bone screw in the seat portion of the respective first and second holes, wherein, along a longitudinal axis of the guide member, the shaft portion has a length greater than a length of the outer surface portion, wherein the through hole of the insert defines an opening at the bottom side of the insert, and wherein the shaft portion and the outer surface portion of the guide member are movable past the opening at the bottom side of the insert to the first position where the shaft portion of the guide member extends past the top side of the insert and the insert is insertable in the first hole of the plate member, wherein the insert comprises a tapered recess between the top side of the insert and the inner wall portion, the tapered recess being increasingly larger in a direction toward the top side of the insert to provide space for movement of the shaft portion of the guide member in the tapered recess during the pivoting movement of the guide member when the guide member is arranged in the insert at the first position, at least a region of the inner wall portion being increasingly larger in a direction toward the bottom side of the insert, the outer surface portion of the guide member being configured to engage the region of the inner wall portion during the pivoting movement of the guide member, and wherein the seat portion of each of the first hole and the second hole has a spherical-segment shape, and the bone screw comprises a head portion having a spherical-segment shape corresponding to the spherical-segment shape of the seat portion of each of the first hole and the second hole.

19. The system of claim 18, wherein:
the insert is assembled in the first hole of the plate and the guide member is inserted into the through hole of the insert, such that the insert is interposed between the guide member and the seat portion of the first hole.

20. The system of claim 18, wherein:
the insert includes a hollow spherical segment-shaped portion extending from a second end of the threaded outer surface portion that has at least one slot to permit the spherical segment-shaped portion to flex in a radial direction, the spherical segment-shaped portion configured to extend below the internal threaded portion of the plate and extend into the seat portion of the plate member;

wherein when the insert is positioned in the internal threaded portion of one of the first and second screw holes, the spherical-segment shaped portion of the insert prevents contact between the spherical segment shaped outer surface portion of the guide member and the seat portion of the one of the first and second holes in the plate.

21. A bone plate system, comprising:
a plate member with a top side, a bottom side and a first hole and a second hole extending through the plate member from the top side to the bottom side, each of the first hole and the second hole including an inner wall portion comprising an internal threaded portion, a seat portion between the internal threaded portion and the bottom side, the seat portion having a spherical-segment shape, and a diameter smaller than a smallest diameter of the internal threaded portion;

an insert configured to be arranged in each of the first hole and the second hole, the insert having a through hole and an inner wall portion defining at least a portion of the through hole of the insert, the insert further including a threaded outer surface portion configured to screw into the internal threaded portion, and a non-threaded outer surface portion extending from a first end of the threaded outer surface portion, wherein when the threaded outer surface portion is fully screwed into the internal threaded portion of the plate member, the first end of the threaded outer surface portion is configured to be substantially flush with the top side of the plate member, and the non-threaded outer surface portion is configured to extend out of the top side of the plate member, the insert further including a hollow spherical segment-shaped portion extending from a second end of the threaded outer surface portion that has at least one slot to permit the spherical segment-shaped portion to flex in a radial direction, the spherical segment-shaped portion configured to extend below the internal threaded portion of the plate and extend into the seat portion of the plate member;

a guide member configured to be removably arranged in the through hole of the insert, the guide member comprising a guide channel and a spherical-segment shaped outer surface portion configured to engage the inner wall portion of the insert so as to allow a pivoting movement of the guide member when the guide member is arranged in the through hole of the insert and such that the spherical-segment shaped outer surface portion is arranged in the seat portion when the guide member is arranged in the through hole of the insert and the insert is arranged in the first hole, the guide member further comprising a shaft portion monolithic with and extending away from the spherical-segment shaped outer surface portion in a direction from the bottom side toward the top side, the guide channel extending through the shaft portion, wherein when the insert is positioned in the internal threaded portion of one of the first and second screw holes, the spherical-segment shaped portion of the insert prevents contact between the spherical segment shaped outer surface portion of the guide member and the seat portion of the one of the first and second holes in the plate;

a bone screw having a head portion in a spherical-segment shape corresponding to the spherical-segment shape of the seat portion such that the head portion is configured to be arranged in the seat portion to anchor the plate member to a bone, the head portion of the bone screw substantially located below the top side of the plate member when axially arranged in the seat portion; and a locking member configured to screw into the internal threaded portion to lock the bone screw in the seat portion.

22. The bone plate system of claim 21, wherein a portion of the shaft portion projects out of the top side of the plate member.

23. The bone plate system of claim 21, further comprising a bushing removably connectable to the guide member and configured to reduce an internal diameter of the guide channel.

24. The bone plate system of claim 21, wherein the spherical-segment shaped outer surface portion extends continuously from a bottom end of the guide member to the shaft portion along at least one side of the guide member.

25. The bone plate system of claim 21, wherein when the threaded outer surface portion of the insert is screwed into the internal threaded portion, the threaded outer surface portion is positionable entirely between the top side and the bottom side of the plate member in an axial direction.

26. The system of claim 21, wherein:
the insert is assembled in the first hole of the plate and the guide member is inserted into the through hole of the insert, such that the insert is interposed between the guide member and the seat portion of the first hole.

27. A bone plate assembly, comprising:
a plate member with a top side, a bottom side and a first hole and a second hole each extending through the plate member from the top side to the bottom side, the first hole and the second hole each including an inner wall portion comprising an internal threaded portion, a seat portion between the internal threaded portion and the bottom side, and a diameter smaller than a smallest diameter of the internal threaded portion;

an insert arranged in one of the first hole and the second hole, the insert having a top surface, a bottom surface, a through hole and an inner wall portion defining at least a portion of the through hole of the insert, the insert including a threaded outer surface portion threaded into the internal threaded portion, the threaded outer surface portion having a first end and a second end, wherein when the threaded outer surface portion is fully screwed into the internal threaded portion of the plate member with the second end directed towards the seat portion of the plate member, the top surface is substantially flush with the top side of the plate member such that an entirety of the insert does not protrude above the top side of the plate member; and a guide member comprising a guide channel and a spherical-segment shaped outer surface portion engaging the inner wall portion of the insert so as to allow a pivoting movement of the guide member relative to the through hole of the insert and such that the spherical-segment shaped outer surface portion is arranged at the seat portion when the guide member is arranged in the through hole of the insert and the insert is arranged in the first hole of the plate member, the guide member further comprising a shaft portion monolithic with and extending away from the spherical-segment shaped outer surface portion, the guide channel extending through the shaft portion, wherein the insert comprises a tapered recess between the top surface of the insert and the inner wall portion, the tapered recess being increasingly larger in a direction toward the top surface of the insert to provide space for movement of the shaft portion of the guide member in the tapered recess during the pivoting movement of the guide member when the guide member is arranged in the insert, at least a region of the inner wall portion being increasingly larger in a direction toward the bottom surface of the insert, the spherical-segment shaped outer surface portion of the guide member being configured to engage the region of the inner wall portion during the pivoting movement of the guide member.

* * * * *